US008685469B2

(12) United States Patent
Shode et al.

(10) Patent No.: US 8,685,469 B2
(45) Date of Patent: Apr. 1, 2014

(54) IN VITRO ANTI-SICKLING ACTIVITY OF BETULINIC ACID, OLEANOLIC ACID AND THEIR DERIVATIVES

(75) Inventors: Francis Oluwole Shode, Westville North (ZA); Neil Koorbanally, Durban (ZA); Pius Tshimankinda Mpiana, Kinshasa (CG); Damien Sha-Tshibey Tshibangu, Kinshasa (CG); Opeoluwa Oyehan Oyedeji, Empangeni (ZA); James Dama Habila, Samaru-Zaria (NG)

(73) Assignee: University of KwaZulu-Natal (ZA)

( * ) Notice: Subject to any disclaimer, the term of this patent is extended or adjusted under 35 U.S.C. 154(b) by 0 days.

(21) Appl. No.: 13/512,472

(22) PCT Filed: Nov. 22, 2010

(86) PCT No.: PCT/IB2010/055327
§ 371 (c)(1),
(2), (4) Date: May 29, 2012

(87) PCT Pub. No.: WO2011/064710
PCT Pub. Date: Jun. 3, 2011

(65) Prior Publication Data
US 2012/0237629 A1  Sep. 20, 2012

(30) Foreign Application Priority Data
Nov. 30, 2009 (ZA) .................................. 2009/08467

(51) Int. Cl.
*A01N 65/00* (2009.01)

(52) U.S. Cl.
USPC ........................................................ 424/725

(58) Field of Classification Search
None
See application file for complete search history.

(56) References Cited

FOREIGN PATENT DOCUMENTS

| WO | WO 2005/076924 | 8/2005 |
|---|---|---|
| WO | WO 03/011891 | 2/2013 |
| ZA | 2005001237 | * 9/2005 |

OTHER PUBLICATIONS

Andesanwo et al. Antisecretory and antiulcerogenic activities of the stem bark extract of *Melaleuca bracteata* and isolation of principles. J Medicinal Plant Res. vol. 3, No. 10, Oct. 1, 2009, pp. 822-824.
Beuzard et al. Eds. (1986) In Approaches to the therapy of sickle cell anaemia, Les Edition Inserum: Paris, 141.
Chandramu, et al. Isolation, characterisation and biological activity of betulinic acid and ursolic acid from *Vitex negundo* L. Pytother. Res., (2003) 17(2), 129-134.
Courtejoie, et al. (1992) Laboratoire et Santé. Saint Paul, Kinshasa, DRC.
Dzubak, et al. Pharmacological activities of natural triterpenoids and their therapeutic implications. Narural Product Reports, (2006) 23, 394-411.
Fujioka, et al. (1994) Anti-AIDS agents, 11. Betulinic acid and platonic acid as anti-HIV principles from *Syzygium claviflorum*, and the anti-HIV activity of structurally related triterpenoids. *Journal of Natural Products*, 57 (2), 243-247.
Fulda, S. Betulinic acid for cancer treatment and prevention. *Int. J. Mol. Sci.*, (2008) 9, 1096-1107.
International Search Report and Written Opinion dated Feb. 17, 2011, received in International Patent Application No. PCT/IB2010/055327.
Mehanna, A.S. Sickle Cell anaemia and Antisickling Agents Them and Now. *Current Medicinal Chemistry*, (2001) 8 (2), 79-88.
Misra, M. The key to medicinal plants research revolves around the detection, isolation, and characterization of antioxidants as the therapeutic agents. J Medicinal Plant Res; vol. 3, No. 10, Oct. 1, 2009, p. 8PP.
Mpiana, et al. Antisickling activity of anthocyanins from Bombax pentadrum, *Ficus capensis* and *Ziziphus mucronata*; Photodegradation effect. J Ethnopharmacology, vol. 120, No. 3, Dec. 8, 2008, pp. 413-318.
Mpiana, et al. In vitro antidrecanocytary activity (anti-sickle cell anaemia) of some Congolese plants. *Phytomedicine*, (2007) 14, 192-195.
Reyes-Zurita, et al. (2009) Maslinic acid, a natural triterpene from *Olea europaea* L., induces apoptosis in HT29 human colon-cancer cells via mitchondrial apoptotic pathway, *Cancer Letters*, 273, 44-54.
Kokkini et al. In: Development of therapeutic agents for sickle cell disease. Rosa, R., Beuzard, Y., Hercules, J. Eds., North-Holland Publishing Co., Amsterdam, (1979) 111-117.
Sarr et al. In vitro modulation of tracheal smooth muscle reactivity by extracts of some Senegalese medicinal plants. J Medicinal Plant Research. vol. 4, No. 1, Jan. 4, 2010, p. 013-018.
Schechter, et al.(1987) The Molecular Basis of Blood Diseases, 1$^{st}$ Edition, Stamatoyannopoulos, G., Arthur, W., Ledre, N.P., Majerus, P.W., Eds., W.B Saunders Company, chapter 6, p. 236-272.
Steele, et al. (1999) In vitro and in vivo evaluation of betulinic acid as an antimalarial. *Phytother. Res.*, 13, 115-159.
Yogeeswari, et al. Betulinic acid and its derivatives: A Review on their Biological Properties. *Current Medicinal Chemistry*, (2005) 12 (6), 657-666.
Xing, Hongtao et al, Cucurbitacin D upregulated fetal hemoglobin expression in K562 cells and human erythroid progenitors. Blood (ASH Annual Meeting Abstracts) vol. 110, No. 11, Abstract 3833, Nov. 2007, and 49$^{th}$ Annual Meeting of the American Society of Hematology; Atlanta, GA, Dec. 8-11, 2007.
Sickle Cell Disease, entry on Wikipedia, Printed Oct. 8, 2012, p. 1-16. Found at http://en.wikipedia.org/wiki/Sickle-cell_disease.

* cited by examiner

*Primary Examiner* — Michael Meller
(74) *Attorney, Agent, or Firm* — Knobbe, Martens Olson & Bear, LLP

(57) ABSTRACT

The invention provides triterpenoid compounds selected from betulinic acid, maslinic acid, oleanolic acid, esters thereof and mixtures of any two or more thereof for the treatment of sickle-cell anaemia.

14 Claims, 13 Drawing Sheets

IN VITRO ANTI-SICKLING ACTIVITY OF BETULINIC ACID, OLEANOLIC ACID AND THEIR DERIVATIVES

RELATED APPLICATIONS

This application is the U.S. National Phase filing under 35 U.S.C. §371 of PCT/IB2010/055327, filed Nov. 22, 2010, which designated the United States and was published in English on Jun. 3, 2011, which claims priority under 35 U.S.C. §119(a)-(d) to South African Patent Application No. 2009/08467, filed Nov. 30, 2009.

THIS invention relates to the treatment of sickle-cell disease (SCD). Sickle cell disease is also called sickle-cell anaemia or drepanocytosis. Sickle cell disease is a life-long blood disorder characterised by red blood cells (erythrocytes) that assume an abnormal, rigid, sickle shape as shown in FIG. 1. Sickling decreases the flexibility of the cell and results in a risk of various complications. The root cause of SCD is a single β-globin gene mutation coding for the sickle β-hemoglobin chain. Sickle haemoglobin tetramers polymerise when deoxygenated and consequently damage the sickle erythrocyte[2].

The consequences of this defect are haemolytic anaemia and tissue damage brought about by the blockage of blood vessels by the sickled cells[2]. The complications can be severe and include retarded growth, periodic attacks of pain and progressive organ dysfunction leading in most cases to a much reduced life expectancy.

Sickle cell anaemia (SCA) is currently treated with chemical agents which interfere with the mechanism and/or kinetics of the sickling process. Most of these drugs, unfortunately, have not shown promising success in terms of clinical use. Therefore, there is a need for more definite and effective treatments for the disease. Most of the currently used anti-sickling agents were developed during the 70s and 80s[3,4,5]. Some examples of drugs in clinical use as anti-sickling agents include 5-azacytidine (1), cytosine arabinoside (2), hydroxyurea (3), phenylalanine (4), vanillin (5), 2,2-dimethylchroman-6-yl alkanoic acids (6), and N-acetylcysteine (7), amongst others[2]. Herbal extracts have also been used in African traditional medicine for the symptomatic treatment of SCA[6].

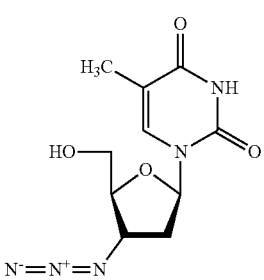

1

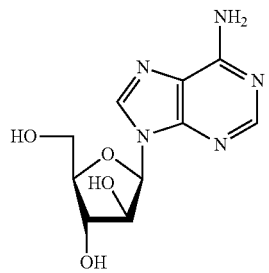

2

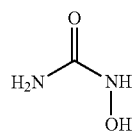

3

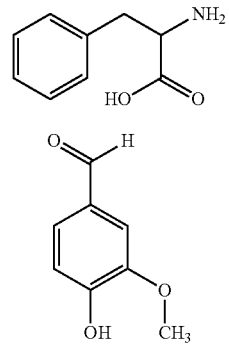

4

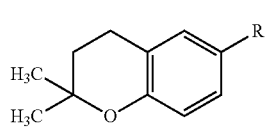

5

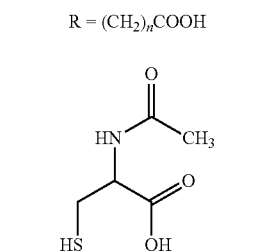

$R = (CH_2)_nCOOH$

6

7

The Applicant has found that triterpenoids from the plant species *Melaleuca bracteata* and the plant species *Syzygium aromaticum* have anti-sickling activity. In particular, the applicant has found that the triterpenoids betulinic acid (8), maslinic acid (10), oleanolic acid (9) and esters thereof have anti-sickling activity.

Betulinic acid (8) was isolated from *Melaleuca bracteata* 'Revolution Gold' leaf extract in good yield (1.7%)[8] and oleanolic acid (9) and maslinic acid (10) were isolated in good to moderate yields from cloves of *Syzygium aromaticum*. The acetate of betulinic acid (11) was prepared from the corresponding acid in excellent yield. Betulinic acid (BA)(8) is a natural product with a range of biological activities. These include anticancer[9], anti-HIV[10], anti-bacterial[11], and anti-malarial[12] amongst others[13]. In many cases, derivatives of BA (8) have shown more potent bioactivity[13]. Similarly, oleanolic acid (OA)(9) occurs naturally in many plants[14] and has biological, pharmacological and medicinal activities[14].

Maslinic acid (MA)(10) occurs naturally in some plants and has been found to have anticancer and anti-diabetic properties[15].

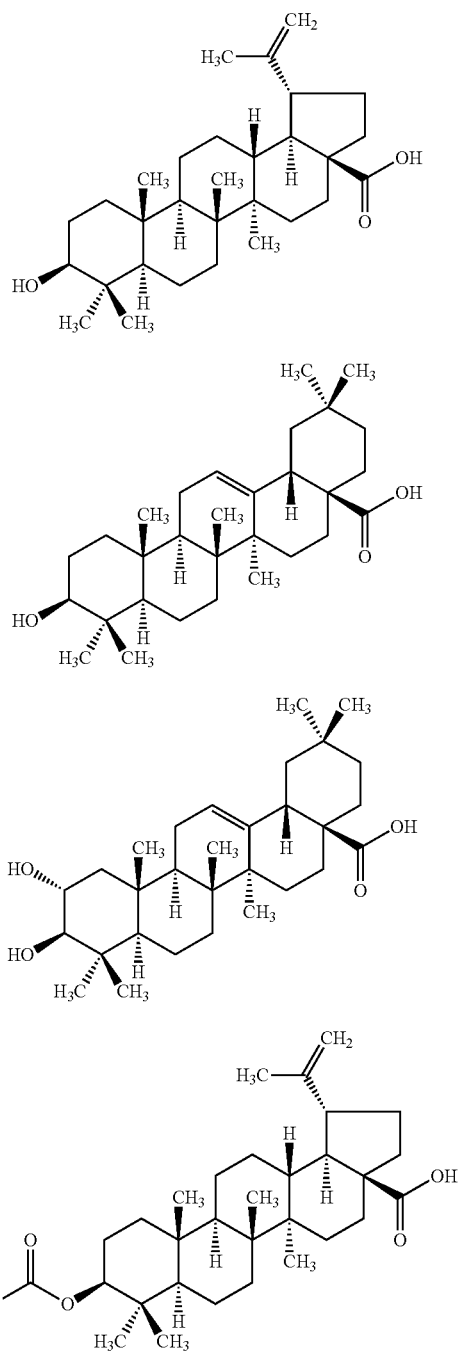

According to a first aspect of the invention, there is provided a triterpenoid compound selected from betulinic acid (8), maslinic acid (10), oleanolic acid (9), esters thereof and mixtures of any two or more thereof for the treatment of sickle-cell anaemia.

According to a second aspect of the invention, there is provided a dosage form for the treatment of sickle-cell anaemia, the dosage form including a triterpenoid compound selected from betulinic acid (8), maslinic acid (10), oleanolic acid (9), esters thereof and mixtures of any two or more thereof.

The, or each, ester may be selected from 2-O-acyl esters, 3-O-acyl esters and mixtures thereof. In particular, the ester may be 3-O-acetoxybetulinic acid.

According to a third aspect of the invention, there is provided a plant extract produced by extracting plant material of plants of the species *Melaleuca bracteata* or *Syzygium aromaticum* or a combination of such plant material or by combining extracts produced by extracting plant material of *Melaleuca bracteata* and *Syzygium aromaticum* for the treatment of sickle-cell anaemia.

According to a fourth aspect of the invention, there is provided a dosage form for the treatment of sickle-cell anaemia, the dosage form including an extract produced by extracting plant material of plants of the species *Melaleuca bracteata* or *Syzygium aromaticum* or a combination of such material or by combining extracts produced by extracting plant material of *Melaleuca bracteata* and *Syzygium aromaticum*.

The plants of the species *Melaleuca bracteata* may be of the variety Revolution Gold.

The extract may be an organic extract. The organic extract may be produced by extracting the plant material with one or more solvents selected from hexane, ethyl acetate and dichloromethane.

The plant material may be selected from material obtained from the leaves of the plant species *Melaleuca bracteata*, material obtained from the dried buds or cloves of the plant species *Syzygium aromaticum* or combinations thereof.

The invention extends to the use of a compound selected from betulinic acid (8), maslinic acid (10), oleanolic acid (9), esters thereof and mixtures of any two or more thereof in the preparation of a medicament for the treatment of sickle-cell anaemia.

The invention extends further to a method of treating sickle-cell anaemia, the method including the step of administering a pharmaceutically effective amount of a compound selected from betulinic acid (8), maslinic acid (10), oleanolic acid (9), esters thereof and mixtures of any two or more thereof to a subject in need of treatment.

The invention extends still further to a dosage form for the treatment of sickle-cell anaemia, the dosage form including a compound selected from betulinic acid (8), maslinic acid (10), oleanolic acid (9), esters thereof and mixtures of any two or more thereof.

The invention extends still further to the use of an extract produced by extracting plant material of plants of the species *Melaleuca bracteata* or *Syzygium aromaticum* or a combination of such plant material or by combining extracts produced by extracting plant material of *Melaleuca bracteata* and *Syzygium aromaticum* in the preparation of a medicament for the treatment of sickle-cell anaemia.

The invention extends still further to a method of treating sickle-cell anaemia, the method including the step of administering to a subject in need of treatment a therapeutically effective amount of an extract produced by extracting plant material of plants of the species *Melaleuca bracteata* or *Syzygium aromaticum* or a combination of such plant material or by combining extracts produced by extracting plant material of *Melaleuca bracteata* and *Syzygium aromaticum*.

The extract may be formed by extracting the plant material with a solvent selected from hexane, ethyl acetate and combinations thereof.

The invention is now described, by way of example, with reference to the following examples and figures in which FIG. 1 shows normal red blood cells and sickled red blood cells[1];

EXAMPLE 1

Extraction and Isolation of Betulinic Acid (8)

Leaves of *Melaleuca bracteata* 'Revolution Gold' were collected from trees growing on the Westville Campus, University of KwaZulu-Natal.

The dried leaves were exhaustively extracted with dichloromethane at room temperature by maceration. After evaporation of the solvent from the extract, a dark green solid mass was obtained. This mass was washed with n-hexane twice to remove oily materials leaving behind a light green solid residue. A portion of the residue was subjected to chromatographic separation on silica gel (60-120 mesh) column (20× 5.5 cm). Elution with hexane/ethyl acetate (8:2→7:3) afforded a cream solid which was re-crystallised from methanol to give a white crystalline material in a yield of 1.07%. The $^1$H NMR and $^{13}$C NMR of the isolated compound were identical with those of an authentic sample of betulinic acid (8).

EXAMPLE 2

Extraction and Isolation of Oleanolic Acid (9) and Maslinic Acid (10) from Cloves

Figure 3:
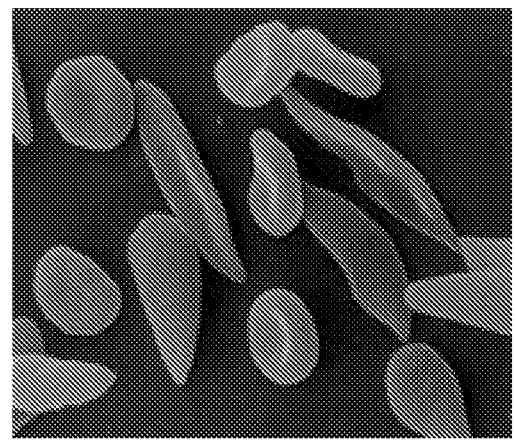
FIG. 3 shows HbS blood after treatment with BA (8), 3-acetoxybetulinic acid (11), and maslinic acid.
Figure 2:
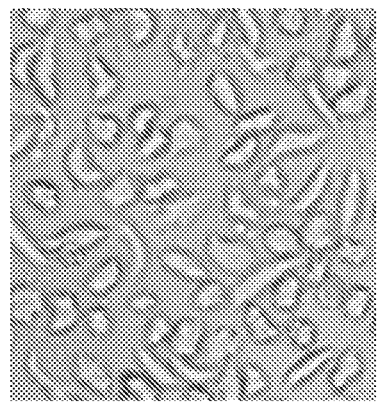
FIG. 2 shows HbS blood before treatment (standard)
Figure 1:
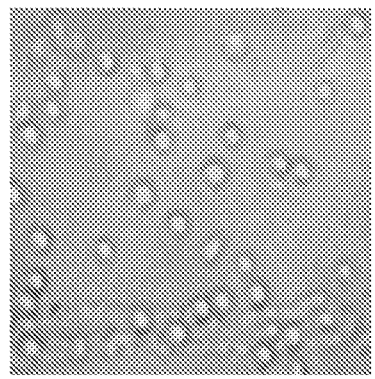
Figure 4:
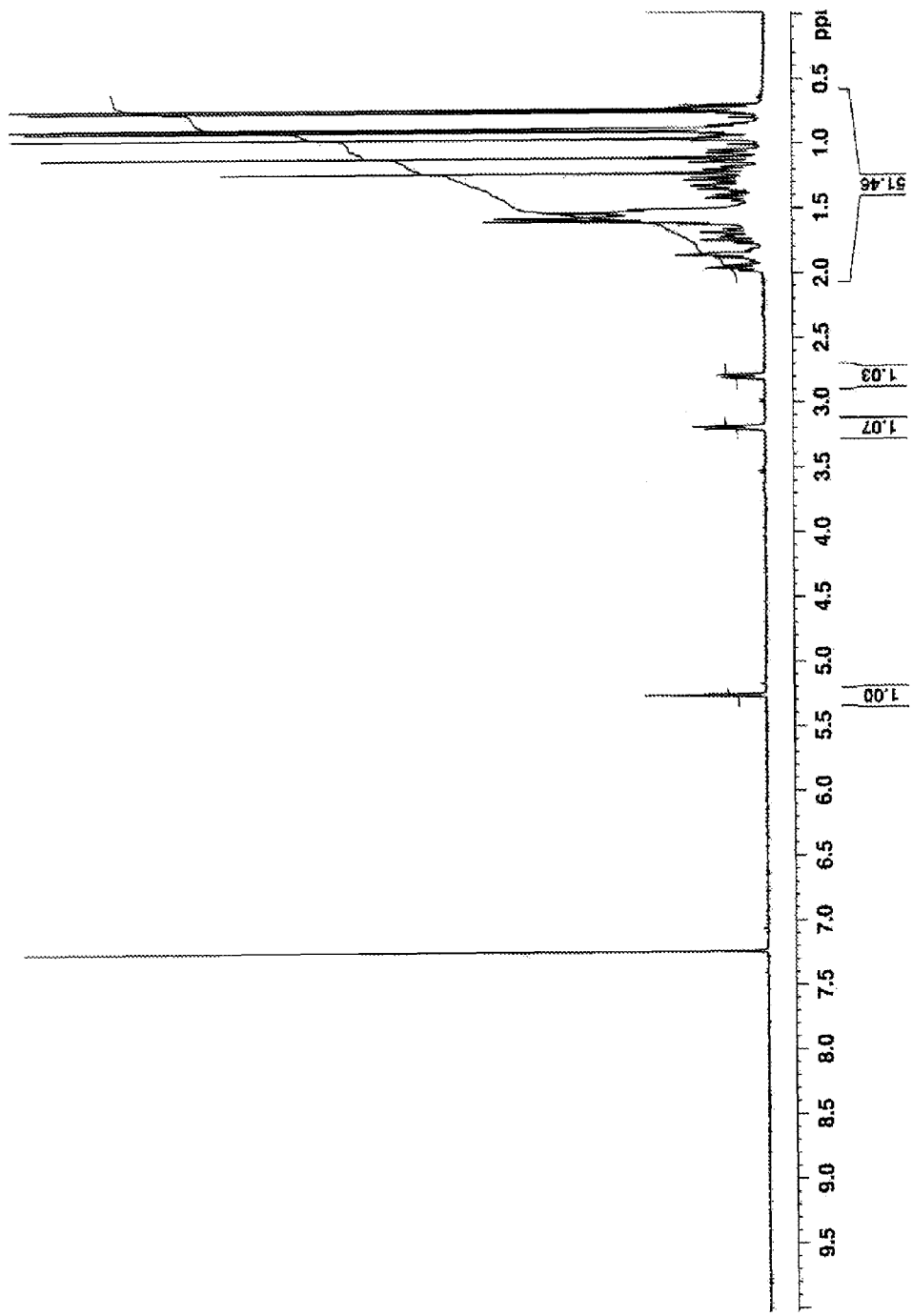
FIG. 4 shows the $^1$H NMR spectrum of oleanolic acid.
Figure 5:
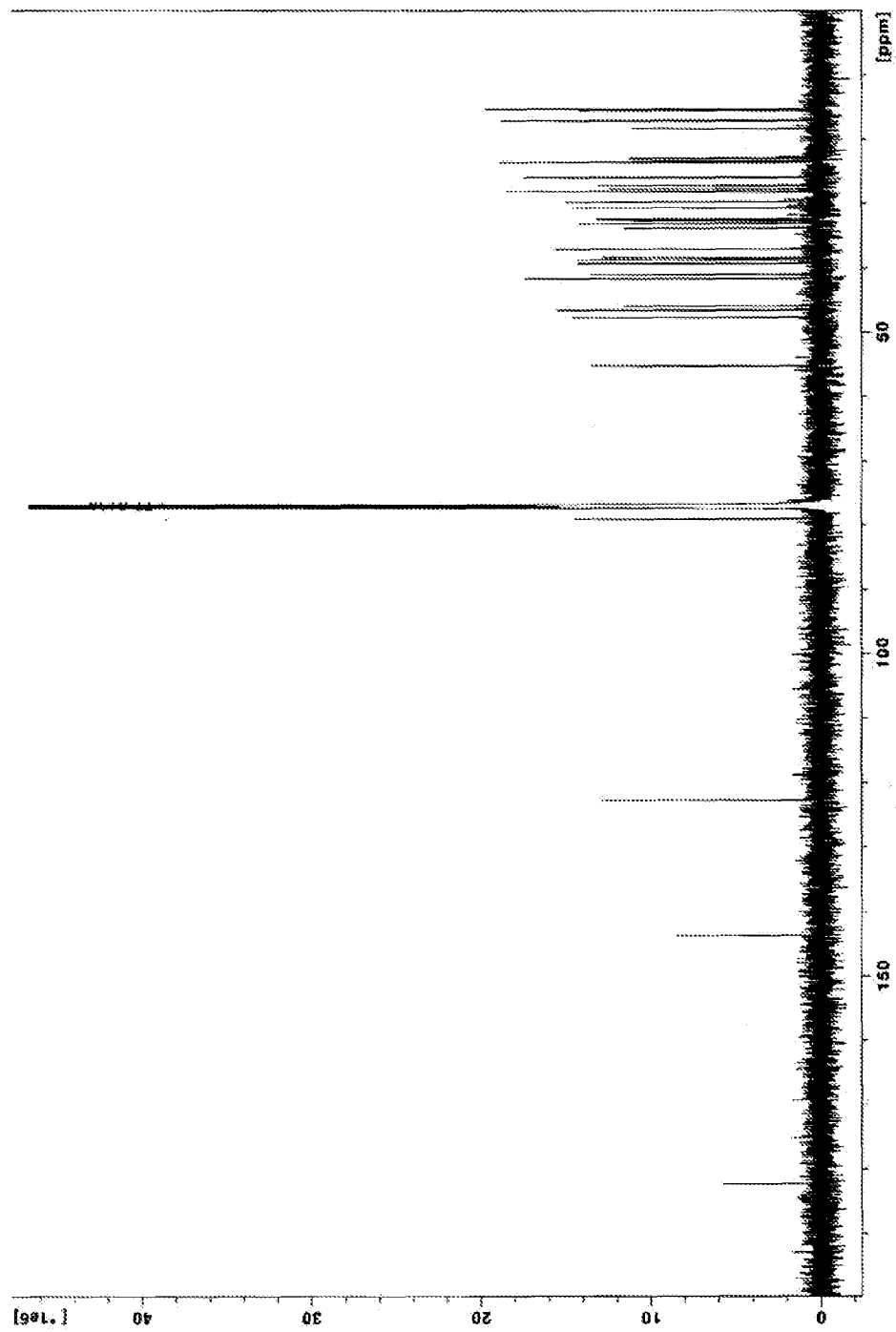
FIG. 5 shows the $^{13}$C NMR spectrum of oleanolic acid.
Figure 6:
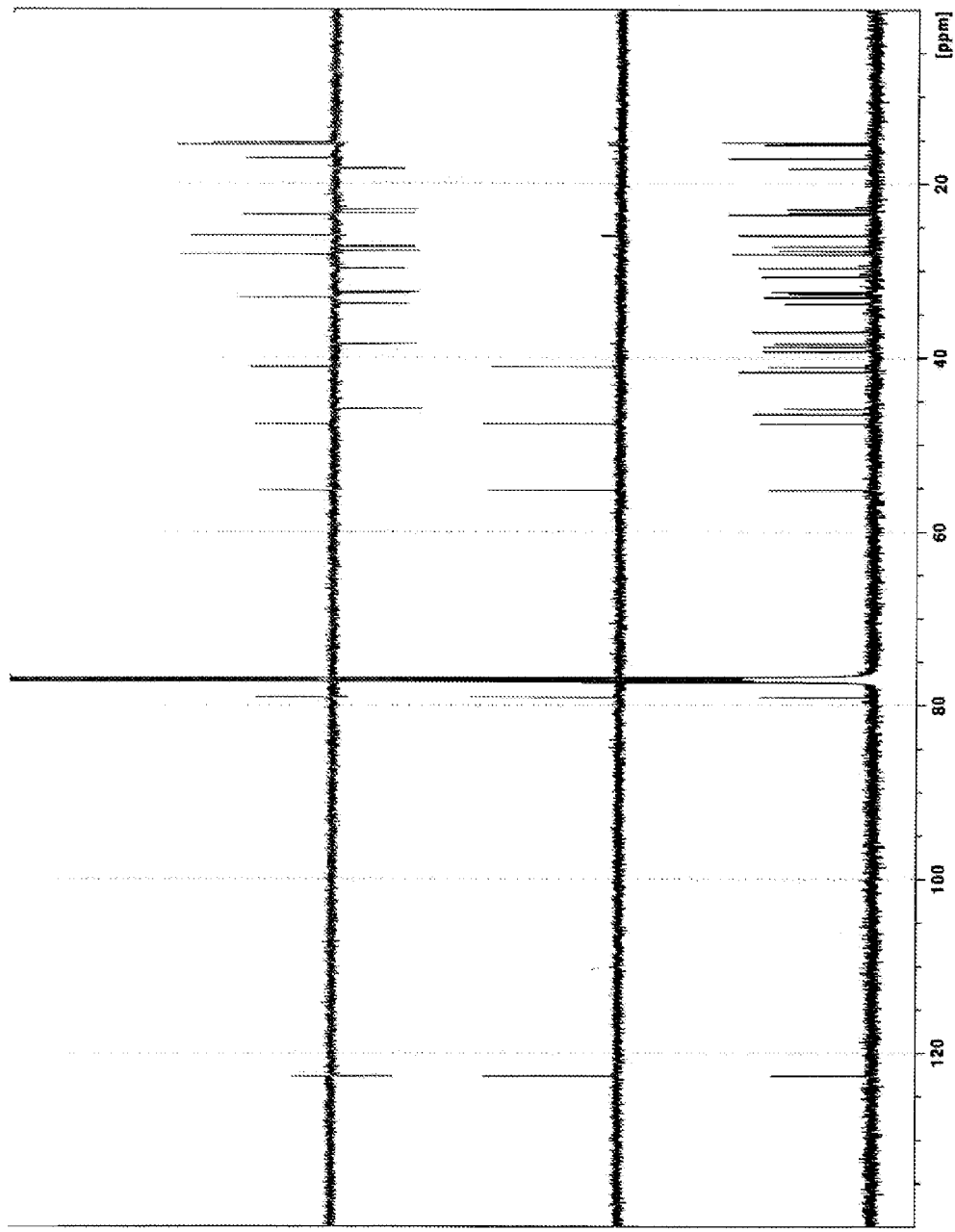
FIG. 6 shows the $^{13}$C DEPT NMR spectrum of oleanolic acid.
Figure 7:
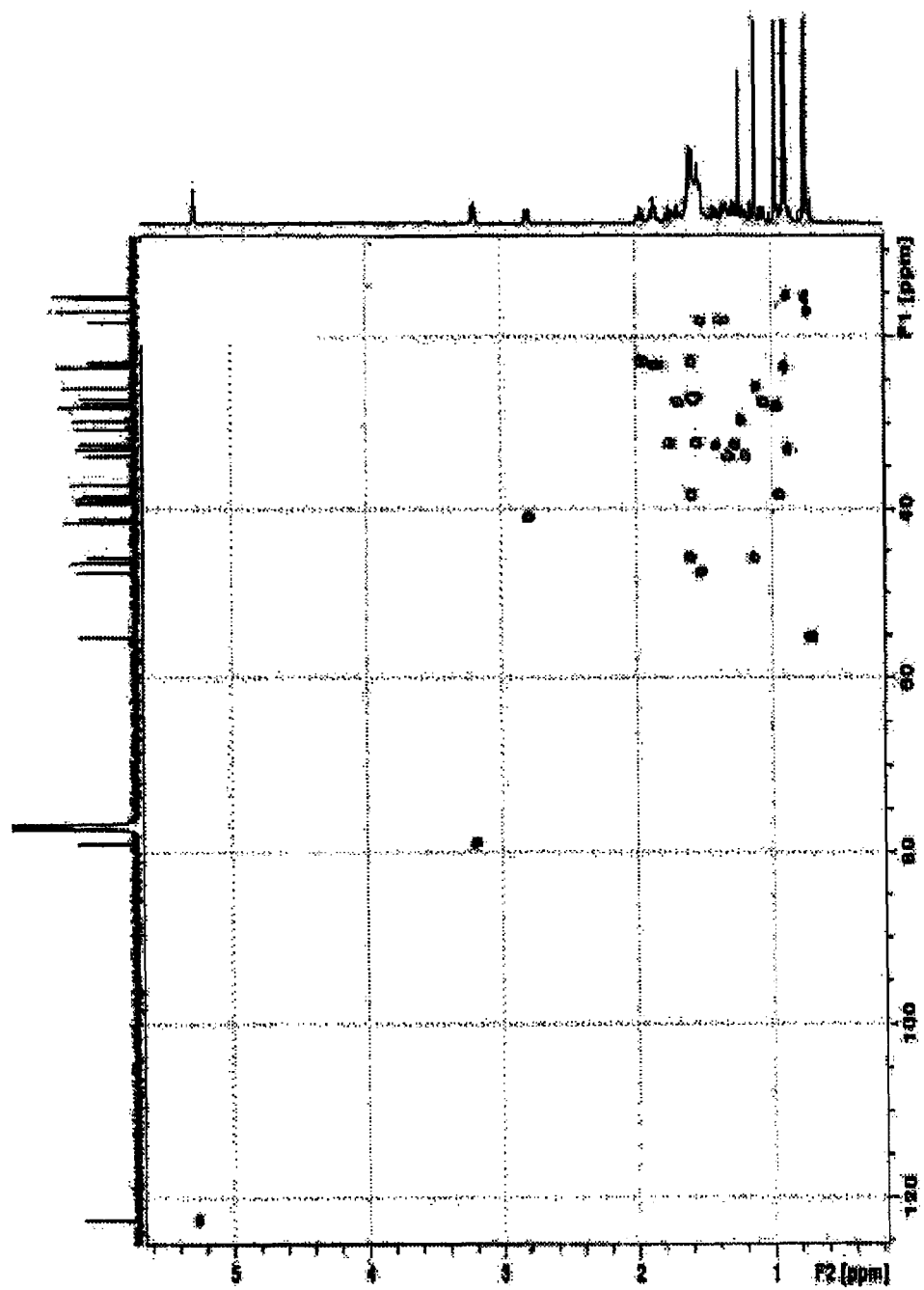
FIG. 7 shows the $^1$H $^{13}$C HSQC NMR spectrum of oleanolic acid.
Figure 8:
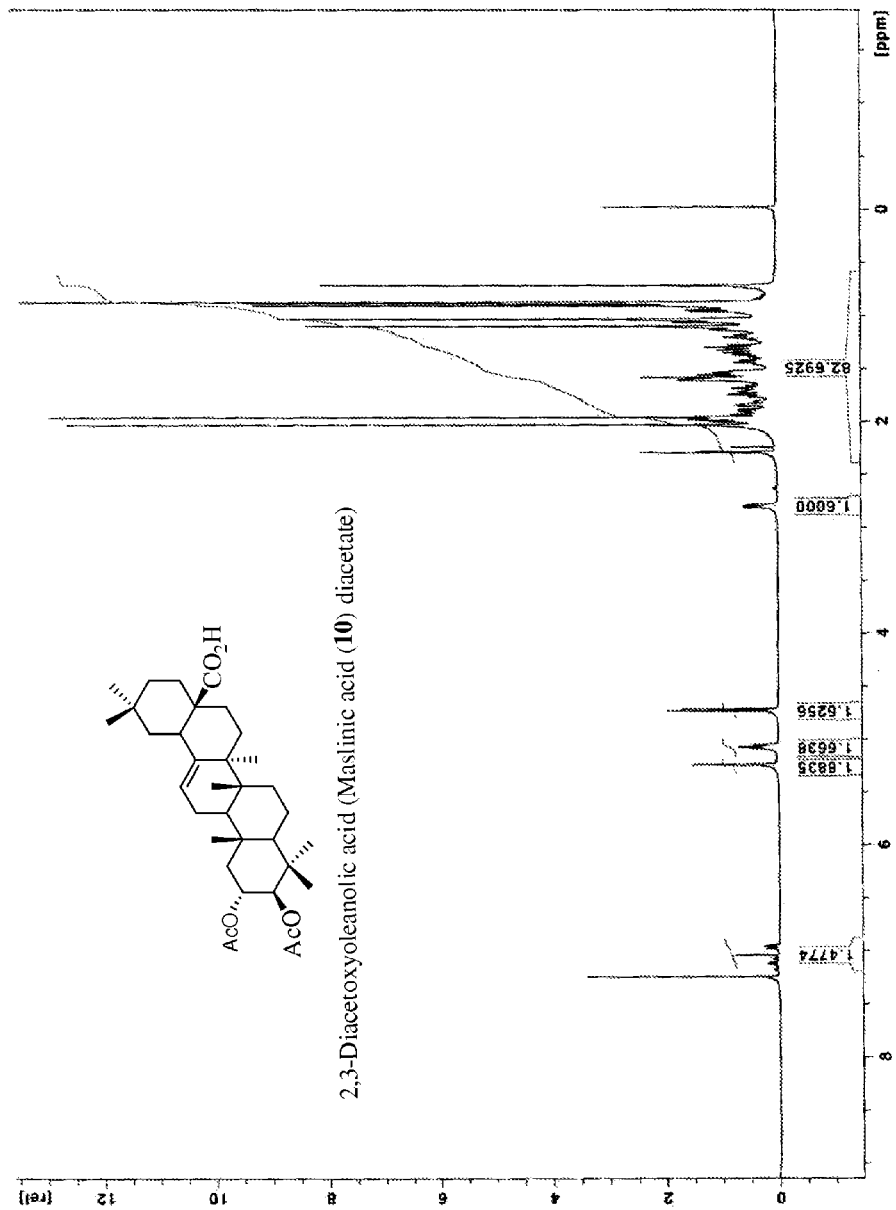
FIG. 8 shows the $^1$H NMR spectrum of maslinic acid diacetate.
Figure 9:
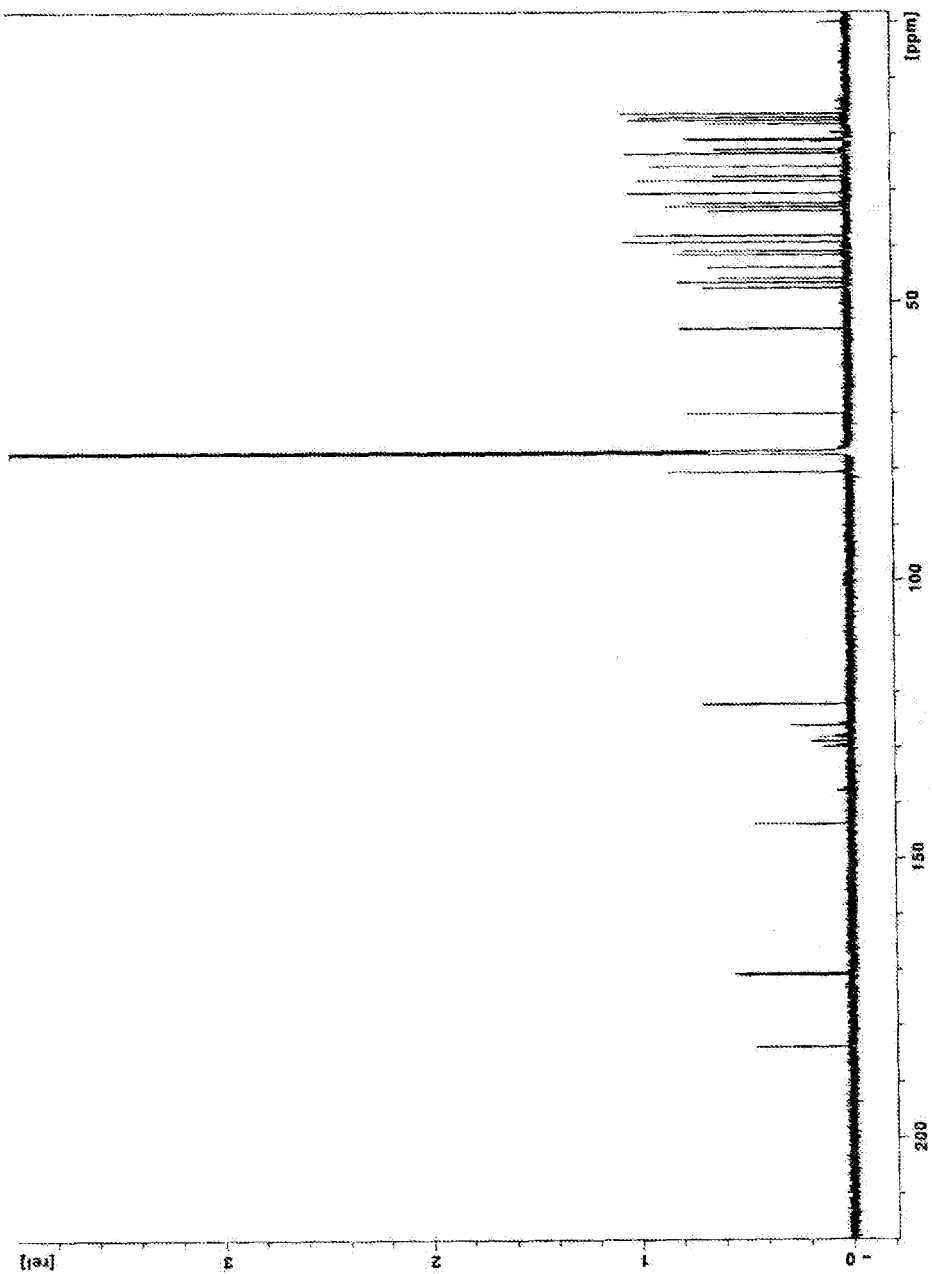
FIG. 9 shows the $^{13}$C NMR spectrum of maslinic acid diacetate.
Figure 10:
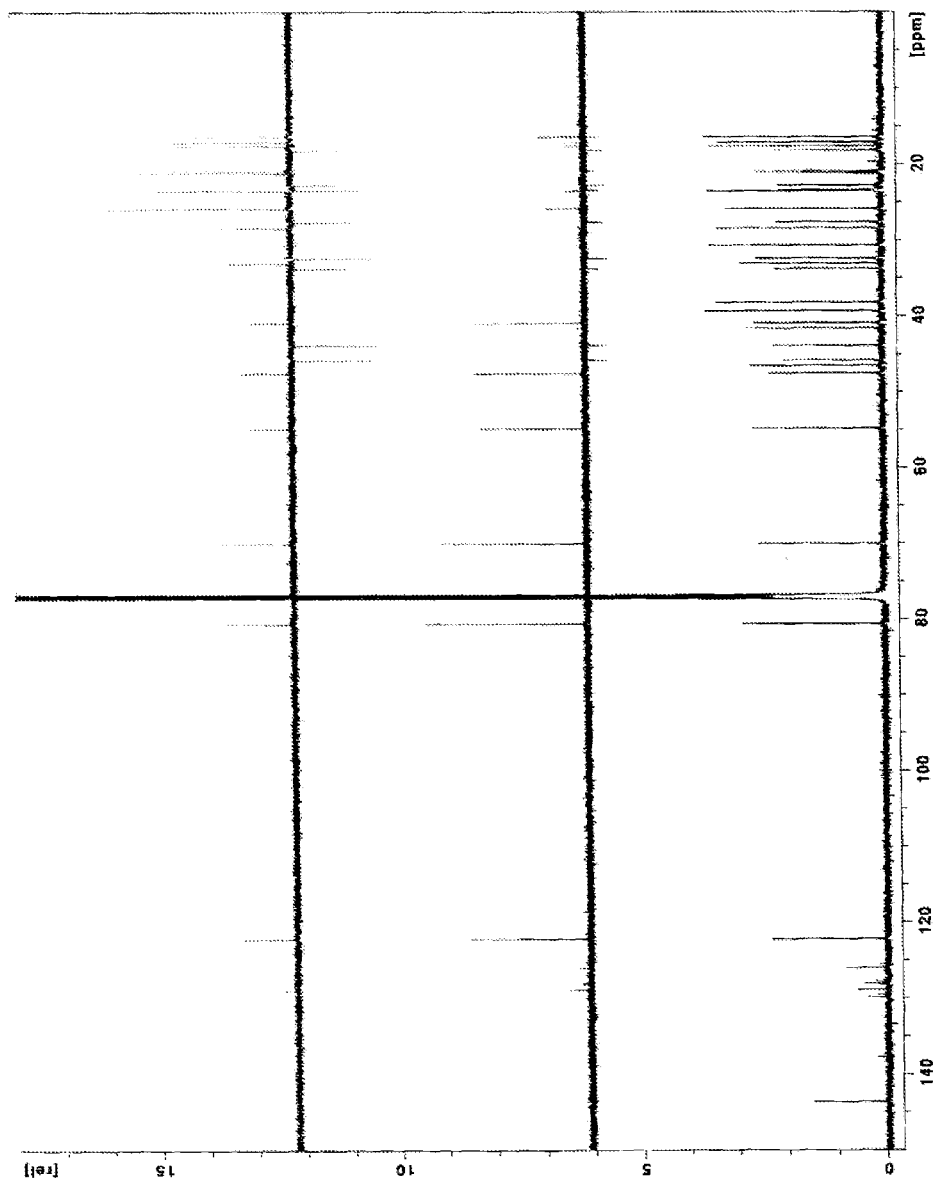
FIG. 10 shows the $^{13}$C DEPT NMR spectrum of maslinic acid.
Figure 11:
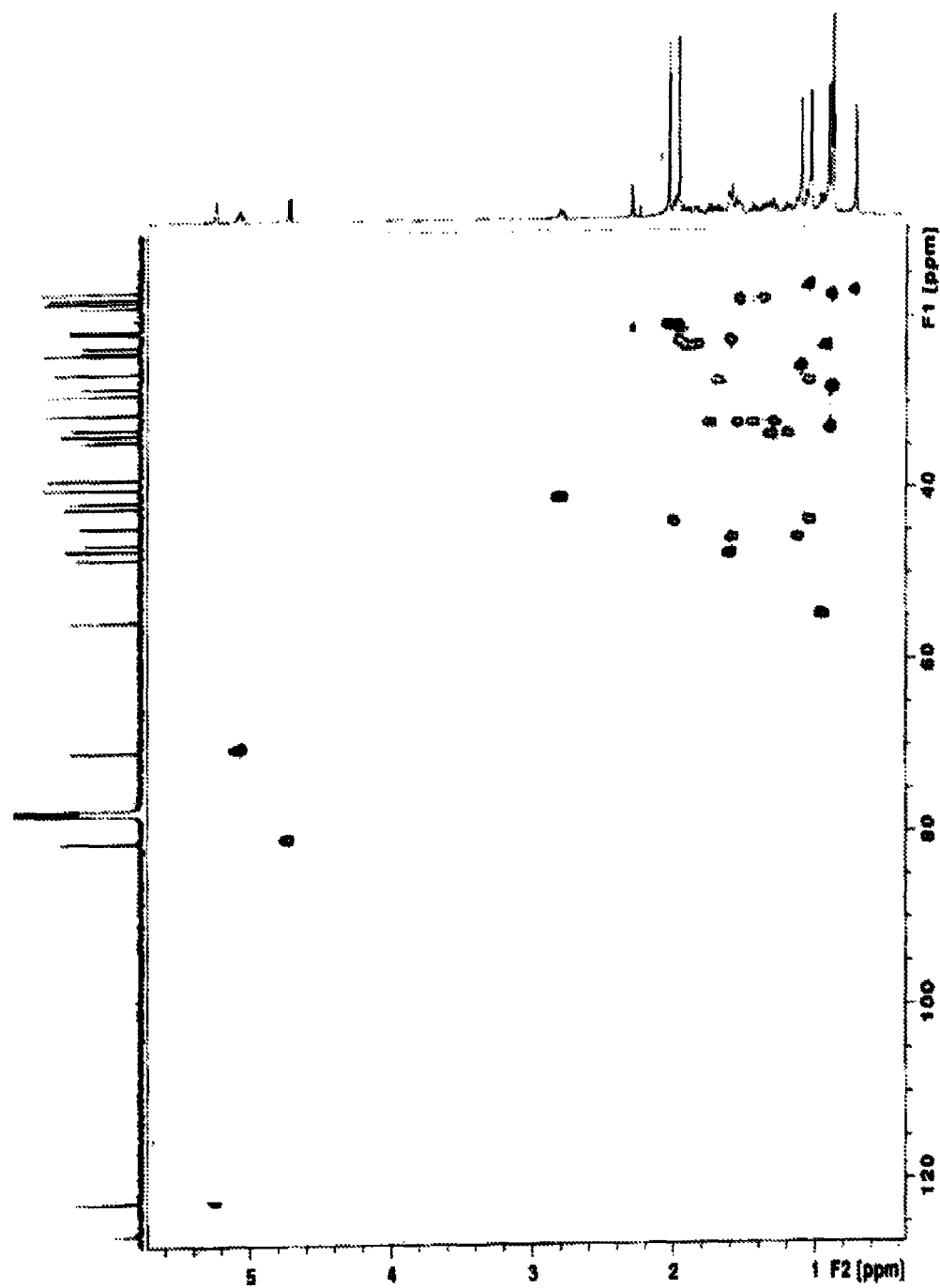
FIG. 11 shows the $^1$H $^{13}$C HSQC NMR spectrum of maslinic acid.

*Syzygium aromaticum* dried buds or whole cloves were obtained commercially. The cloves (1.5 kg, whole) of *Syzygium aromaticum* were sequentially and exhaustively extracted with hexane and ethyl acetate to give, after solvent removal in vacuo, a hexane extract (68.8 g, 4.9%) and an ethyl acetate extract (34.1 g, 2.3%). A portion of the ethyl acetate extract (10.0 g), was subjected to chromatographic separation on silica gel (60-120 mesh) column (40×5.0 cm). Elution with hexane/ethyl acetate solvent mixtures (8:2→6:4) afforded pure oleanolic acid (9) (4.7 g, 1.06%), a mixture of oleanolic acid (9) and maslinic acid (10) (0.5 g), and pure maslinic acid (10) (0.25 g). The structures of oleanolic acid (9) and maslinic acid (10) (as 2,3-diacetoxyoleanolic acid) were confirmed by spectroscopic data analysis (1D and 2D $^1$H NMR and $^{13}$C NMR experiments) (FIGS. 4-7 and FIGS. 8-10, respectively).

EXAMPLE 3

Preparation of 3-acetoxybetulinic Acid (11)

Figure 12:
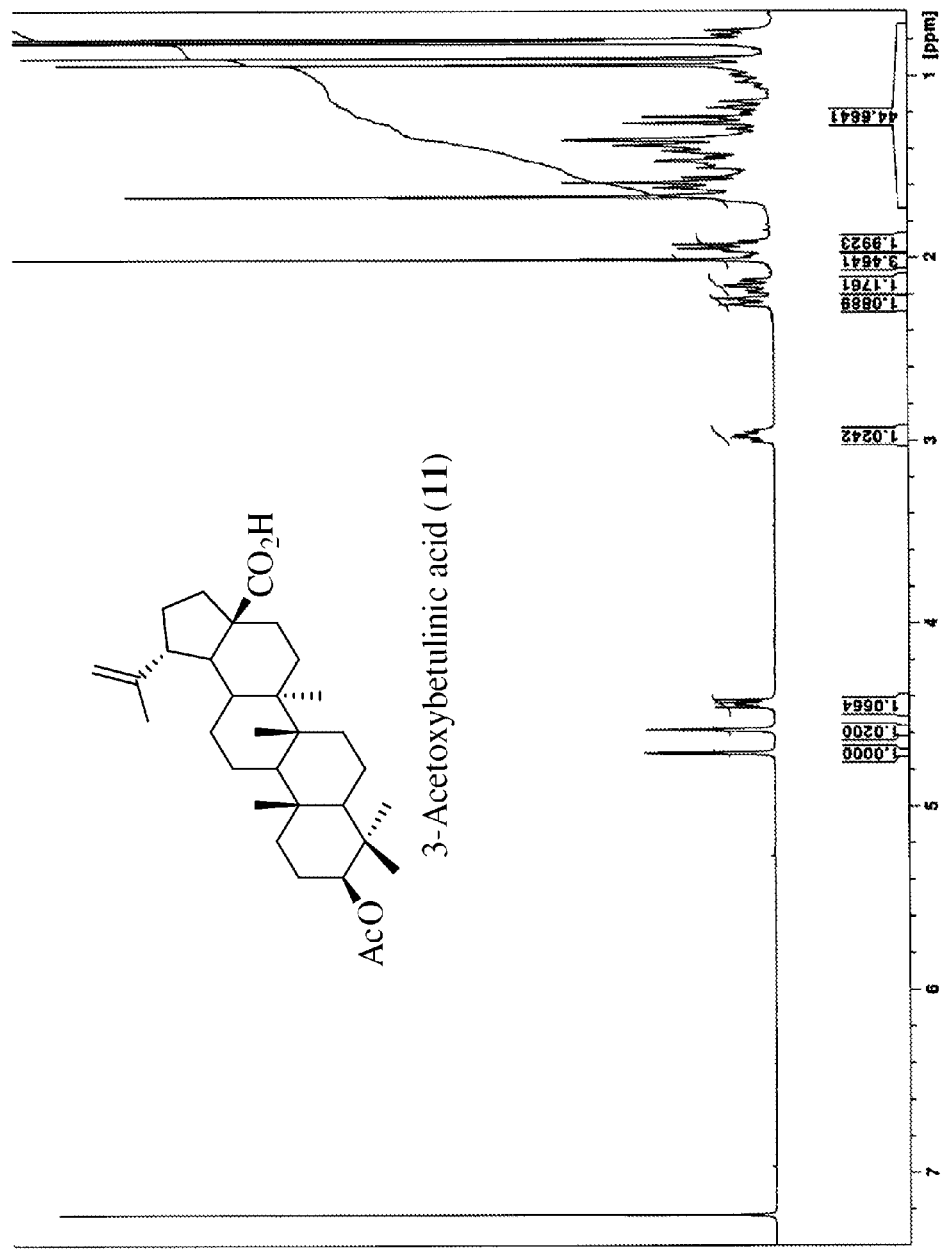
FIG. 12 shows the $^1$H NMR spectrum of 3-acetoxybetulinic acid.
Figure 13:
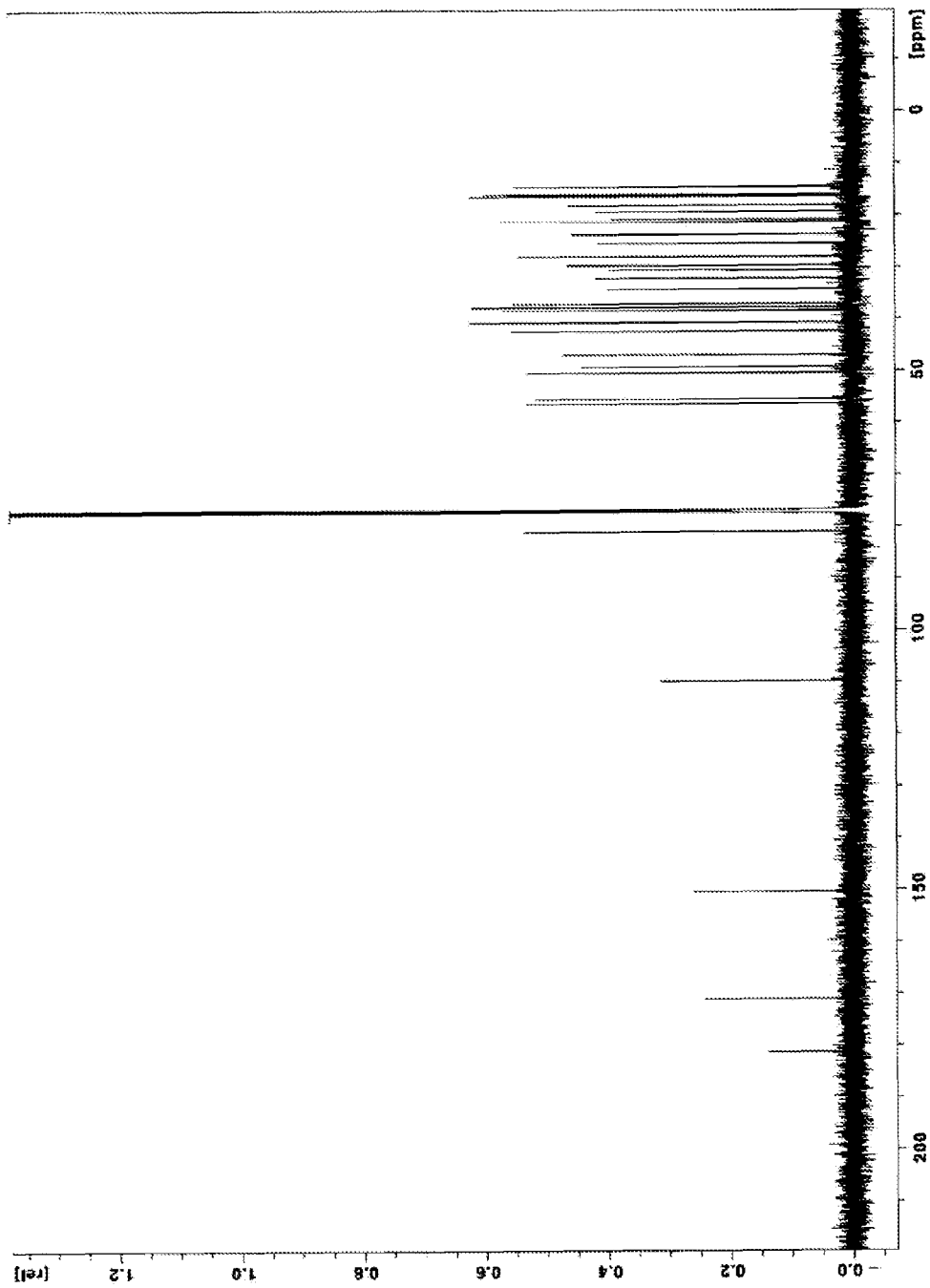
FIG. 13 shows the $^{13}$C NMR spectrum of 3-acetoxybetulinic acid.
Figure 14:
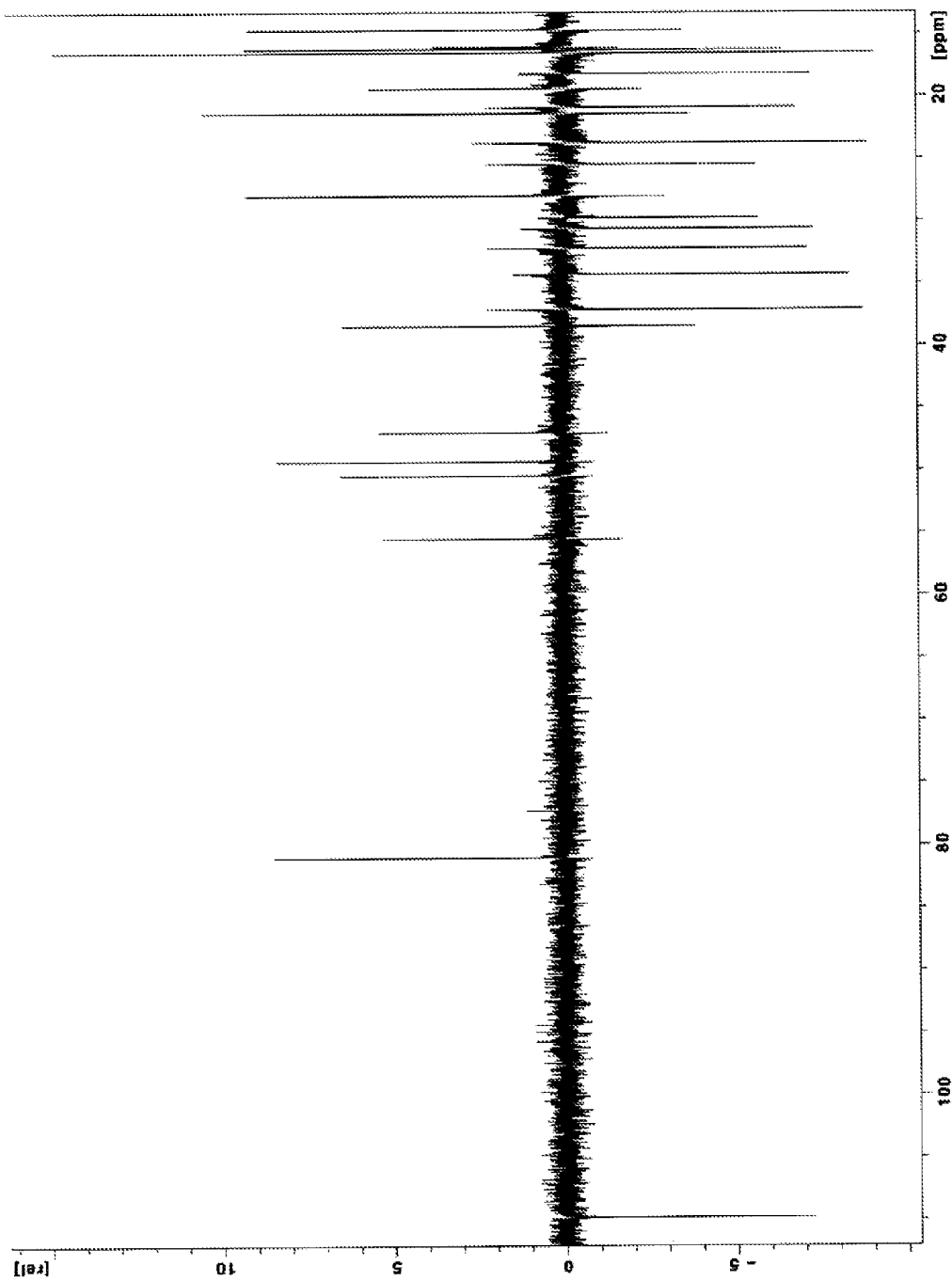
FIG. 14 shows the $^{13}$C DEPT 135° NMR spectrum of 3-acetoxybetulinic acid.
Figure 15:
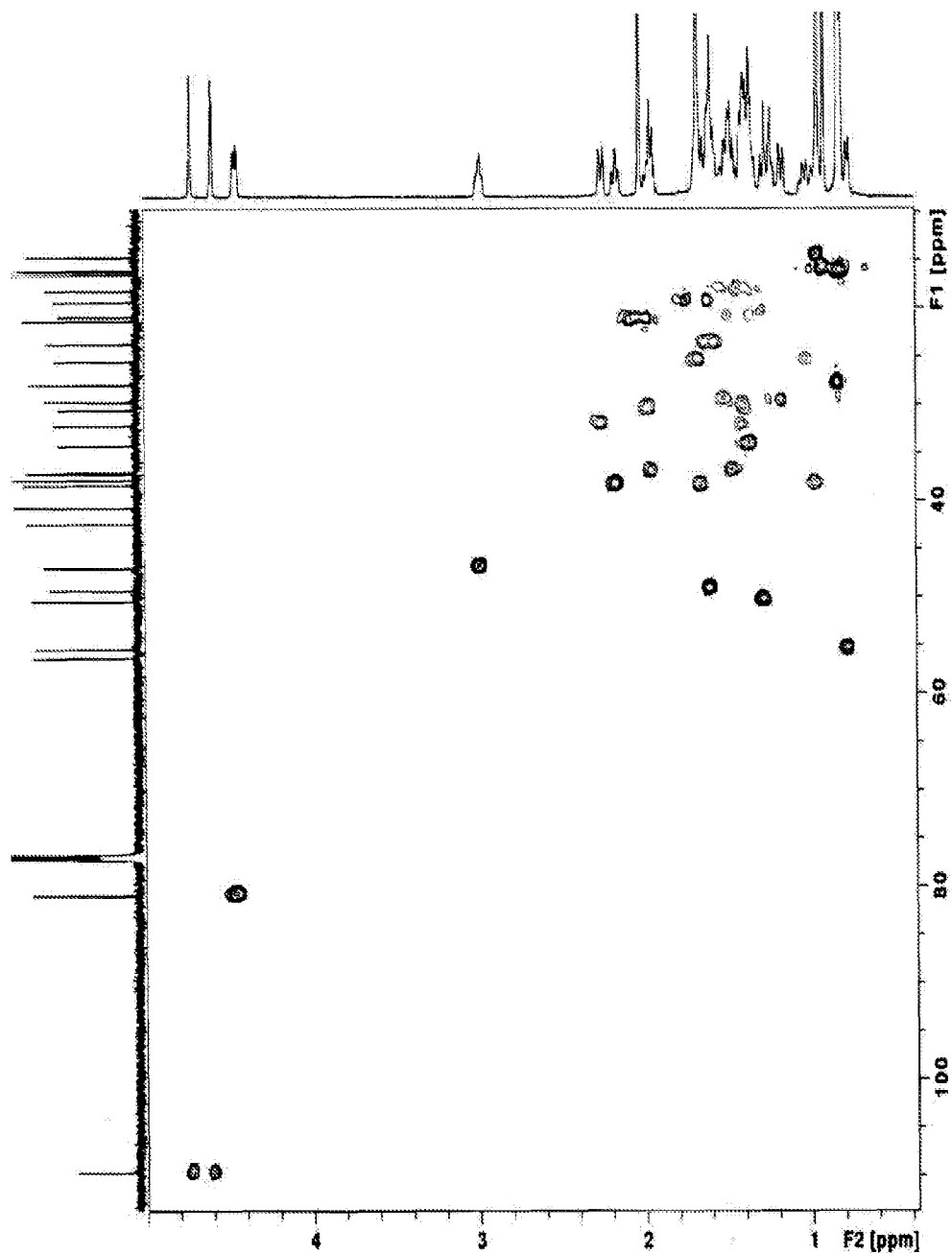
FIG. 15 shows the $^1$H $^{13}$C HSQC NMR spectrum of 3-acetoxybetulinic acid.

A mixture of betulinic acid (8) (1 g), acetic anhydride (10 mL), and pyridine (5 mL) was stirred overnight at room temperature. The reaction mixture was poured into water and stirred for 30 minutes. A solid formed and was filtered and re-crystallized from ethyl acetate to give pure crystals of 3-acetoxybetulinic acid (11) in good yield. The structure of the acetate was confirmed by spectroscopic data analysis (FIG. 12-15) and comparison with an authentic sample.

EXAMPLE 4

Biological Tests

Blood samples were collected from "Centre de Medecine Mixte et d'Anémie SS" located in Kinshasa, Democratic Republic of Congo (DRC). The blood samples were first characterised by Hb electrophoresis on cellulose acetate gel, in order to confirm their SS nature, as previously reported by Mpiana et al., 2007[6]. Confirmed SS blood samples were refrigerated at ~4° C., and used for Emmel test.

Emmel Test

A drop of physiological solution was put on a glass slide and a drop of SS blood was added on the physiological solution. One drop of 2% sodium metabisulphite solution was added on the slide glass which was hermetically covered using a cover glass with melted paraffin wax and kept covered for 2 hours in order to accelerate the sickling of the blood. After 2 hours in anaerobic conditions, the blood sample became deoxygenated and adopted sickle shape. Assay was observed under an optical microscope and the number of observed erythrocytes was determined using Thomas' cell (Courtejoie, J. and Hartaing, I, 1992)[7].

Biological Activity

SS blood samples were contacted at different concentrations with diluted samples of the compounds (8), (9), (10), and (11) using physiological solution (NaCl 0.9%) as dilution solvent, according to Emmel's test procedure as reported above and optical measurements were taken.

Data Analysis

Pictures were obtained with an optical microscope (motic). In order to convert the photonic micrograph image into a digital image, a Canon digital camera (Zoom X6) was used to digitize micrographs using Motic Images 200 version 1.3 software, on Windows XP. Thomas' cell was used to observe the number of erythrocytes. The results of the in vitro anti-sickling activity of betulinic acid (8), 3-acetoxybetulinic acid (11), oleanolic acid (9) and maslinic acid (10) are shown in Table 1.

TABLE 1

In vitro anti-sickling effects of betulinic acid (8), 3-acetoxybetulinic acid (11), oleanolic acid (9), and maslinic acid (10) using Emmel Test

| Sample Code | Chemical Name | Emmel Test Result |
|---|---|---|
| DS/10/C/A | Betulinic acid | +++ |
| DS/10/C/Ab | 3-acetoxybetulinic acid | +++ |

TABLE 1-continued

In vitro anti-sickling effects of betulinic acid (8), 3-acetoxybetulinic acid (11), oleanolic acid (9), and maslinic acid (10) using Emmel Test

| Sample Code | Chemical Name | Emmel Test Result |
| --- | --- | --- |
| DS/FS/1 | Oleanolic acid | + |
| DS/FS/2 | Maslinic acid | +++ |

Legend:
+++ = >70% normalisation of sickled blood cells.;
+ = 10 to 50% normalisation of sickled blood cells.

Oleanolic acid (9) had the lowest activity (10-50% normalisation) whilst betulinic acid (8), 3-acetoxybetulinic acid (11) and maslinic acid (10) had the highest activity (>70% normalisation). This remarkable activity is shown in FIGS. 6a and 6b. It is an advantage of the invention illustrated that betulinic acid (8), 3-acetoxybetulinic acid (11), and maslinic acids (10) have high in vitro anti-sickling activity which can be exploited to develop safe, potent, and cheap anti-sickling agents for the control and management of sickle cell disease (SCD).

REFERENCES

[1] http://en.wikipedia.org/wiki/Sickle-cell disease. Accessed on Nov. 13, 2009.
[2] Mehanna, A. S. (2001) Sickle Cell anaemia and Antisickling Agents Them and Now. *Current Medicinal Chemistry,* 8 (2), 79-88.
[3] Schechter, A. N, Noguchi, C. T., Rodgers, C. P. (1987) In the Molecular Basis of Blood Diseases, 1st Edition, Stamatoyannopoulos, G., Arthur, W., Ledre, N. P., Majerus, P. W., Eds., W.B Saunders Company, chapter 6, 179.
[4] Rosa, J., Beuzard, Y., Hercules, J. (1979) In Development of Therapeutic Agents for Sickle Cell Disease, North-Holand publishing Co., Amsterdam.
[5] Beuzard, Y., Charache, S., Galacteros, F. Eds. (1986) In Approaches to the therapy of sickle cell anaemia, Les Edition Inserum: Paris, 141.
[6] Mpiana, P. T., Tshibangu, D. S. T., Shetonde, O. M., Ngbolua, K. N. (2007) In vitro antidrepanocytary activity (anti-sickle cell anaemia) of some Congolese plants. *Phytomedicine,* 14, 192-195.
[7] Courtejoie, J., Hartaing, I. (1992) Laboratoire et Santé. Saint Paul, Kinshasa, DRC.
[8] Mukherjee, P. K., Pal, M., Saha, B. P. (2003) A process for the isolation of betulinic acid from *Nelumbo nucifera* Gaertn rhizomes. WO 03/011891.
[9] Fulda, S. (2008) Betulinic acid for cancer treatment and prevention. *Int. J. Mol. Sci.,* 9, 1096-1107.
[10] Fujioka, T., Kashiwada, Y., Kilkuskie, R. E., Cosentino, L. M., Ballas, L. M., Jiang, J. B., Janzen, W. P., Chen, I. S., Lee, K. H. (1994) Anti-AIDS agents, 11. Betulinic acid and platonic acid as anti-HIV principles from *Syzygium claviflorum,* and the anti-HIV activity of structurally related triterpenoids. *Journal of Natural Products,* 57 (2), 243-247.
[11] Chandramu, C., Manohar, R. D, Krupadanam, D. G, Dashavantha, R. V., (2003) Isolation, characterisation and biological activity of betulinic acid and ursolic acid from Vitex negundo L. *Pytother. Res.,* 17(2), 129-134.
[12] Steele, J. C., Warhurst, D. C., Kirby, G. C., Simmonds, M. S. (1999) In vitro and in vivo evaluation of betulinic acid as an antimalarial. *Phytother. Res.,* 13, 115-159.
[13] Yogeeswari, P., Dharmarajan, S. (2005) Betulinic acid and its derivatives: A Review on their Biological Properties. *Current Medicinal Chemistry,* 12 (6), 657-666.
[14] Dzubak, P., Hajduch, M., Vydra, D., Hustova, A., Kvasnica, M., Biedermann, D., Markova, L., Urban, M., Sarek, J. (2006) Pharmacological activities of natural triterpenoids and their therapeutic implications. *Narural Product Reports,* 23, 394-411.
[15] Reyes-Zurita, F. J., Rufino-Palomares, E. E., Lupiáñez, J. A., Cascante, M. (2009) Maslinic acid, a natural triterpene from Olea europaea L., induces apoptosis in HT29 human colon-cancer cells via the mitochondrial apoptotic pathway. *Cancer Letters,* 273, 44-54.

The invention claimed is:

1. A composition for the symptomatic treatment of sickle cell disease consisting essentially of a therapeutically effective amount of a dichloromethane extract of *Melaleuca bracteata* variety Revolution Gold.

2. The composition of claim 1, wherein the extract is from the leaves of *Melaleuca bracteata* variety Revolution Gold.

3. A composition for the symptomatic treatment of sickle cell disease consisting essentially of a therapeutically effective amount of a dichloromethane extract of *Melaleuca bracteata* variety Revolution Gold and a therapeutically effective amount of an extract of *Syzygium aromaticum*.

4. The composition of claim 3, wherein the *Melaleuca bracteata* variety Revolution Gold extract is from the leaves.

5. The composition of claim 3, wherein the *Syzygium aromaticum* extract is from the dried buds or cloves or combinations thereof.

6. The composition of claim 4, wherein the *Syzygium aromaticum* extract is from the dried buds or cloves or combinations thereof.

7. The composition of claim 3, wherein the composition consists essentially of a dichloromethane extract of *Melaleuca bracteata* variety Revolution Gold and *Syzygium aromaticum*.

8. The composition of claim 4, wherein the composition consists essentially of a dichloromethane extract of *Melaleuca bracteata* variety Revolution Gold and *Syzygium aromaticum*.

9. The composition of claim 5, wherein the composition consists essentially of a dichloromethane extract of *Melaleuca bracteata* variety Revolution Gold and *Syzygium aromaticum*.

10. The composition of claim 6, wherein the composition consists essentially of a dichloromethane extract of *Melaleuca bracteata* variety Revolution Gold and *Syzygium aromaticum*.

11. The composition of claim 3, wherein the composition consists essentially of a combination of a first dichloromethane extract of *Melaleuca bracteata* variety Revolution Gold and a second extract of *Syzygium aromaticum*.

12. The composition of claim 4, wherein the composition consists essentially of a combination of a first dichloromethane extract of *Melaleuca bracteata* variety Revolution Gold and a second extract of *Syzygium aromaticum*.

13. The composition of claim 5, wherein the composition consists essentially of a combination of a first dichloromethane extract of *Melaleuca bracteata* variety Revolution Gold and a second extract of *Syzygium aromaticum*.

14. The composition of claim 6, wherein the composition consists essentially of a combination of a first dichloromethane extract of *Melaleuca bracteata* variety Revolution Gold and a second extract of *Syzygium aromaticum*.

* * * * *